US012638436B1

(12) United States Patent
Karki et al.

(10) Patent No.: US 12,638,436 B1
(45) Date of Patent: May 26, 2026

(54) PROTECTIVE CASE FOR SOIL MOISTURE METER

(71) Applicant: Earth Scout, GBC, Minneapolis, MN (US)

(72) Inventors: Dipesh Karki, Minneapolis, MN (US); Troy Schmidtke, Minneapolis, MN (US); Christopher Burg, Minneapolis, MN (US); Michael Immer, Minneapolis, MN (US); Peder Lindberg, Fargo, ND (US); Scott Lawton, Eau Claire, WI (US)

(73) Assignee: EarthScout LLC, Brooklyn Park, MN (US)

( * ) Notice: Subject to any disclaimer, the term of this patent is extended or adjusted under 35 U.S.C. 154(b) by 309 days.

(21) Appl. No.: 18/630,306

(22) Filed: Apr. 9, 2024

(51) Int. Cl.
G01N 33/24 (2006.01)

(52) U.S. Cl.
CPC .................................. G01N 33/246 (2013.01)

(58) Field of Classification Search
CPC ...... G01N 33/246; H01R 31/06; H01R 13/58; H01R 43/26; H04B 1/3888
See application file for complete search history.

(56) References Cited

U.S. PATENT DOCUMENTS

| | | | | |
|---|---|---|---|---|
| 4,696,189 | A | * | 9/1987 | Hochreuther .......... G01D 11/24 |
| | | | | 73/431 |
| 4,918,375 | A | | 4/1990 | Malleki et al. |

| | | | | |
|---|---|---|---|---|
| D325,471 | S | * | 4/1992 | McCain .......................... D3/226 |
| 5,136,249 | A | | 8/1992 | White et al. |
| 5,420,517 | A | | 5/1995 | Skaling et al. |
| 6,632,534 | B2 | | 10/2003 | Skaling et al. |
| 6,978,794 | B2 | | 12/2005 | Dukes et al. |
| 9,626,238 | B2 | | 4/2017 | Sheynblat et al. |
| 9,690,426 | B1 | | 6/2017 | Eichwald |
| 10,448,585 | B2 | | 10/2019 | Kundra et al. |
| 10,509,019 | B2 | | 12/2019 | Lee |
| 11,275,949 | B2 | | 3/2022 | Chan et al. |
| 11,360,644 | B2 | | 6/2022 | Karunumunai et al. |
| 11,429,401 | B2 | | 8/2022 | Busekrus et al. |
| 11,614,781 | B1 | | 3/2023 | Publicover et al. |
| 11,652,326 | B2 | * | 5/2023 | Carnevali ............. G06F 1/1632 |
| | | | | 439/533 |
| 11,728,846 | B1 | * | 8/2023 | Carnevali ............ H04B 1/3888 |
| | | | | 455/41.1 |
| 12,126,199 | B2 | * | 10/2024 | Carnevali ............... H02J 7/731 |
| 12,362,527 | B2 | * | 7/2025 | Carnevali .............. H01R 43/26 |
| 2006/0256075 | A1 | | 11/2006 | Anastas et al. |
| 2009/0212789 | A1 | | 8/2009 | Lin et al. |
| 2018/0059014 | A1 | | 3/2018 | Ruback et al. |
| 2018/0368339 | A1 | | 12/2018 | Van Der Lee |
| 2020/0359583 | A1 | | 11/2020 | Buss |
| 2021/0140908 | A1 | | 5/2021 | Van Houweling et al. |

(Continued)

FOREIGN PATENT DOCUMENTS

BR          PI0905016 A2 * 11/2010

*Primary Examiner* — Francis C Gray
(74) *Attorney, Agent, or Firm* — Dietz Law Office LLC

(57) ABSTRACT

A protective case for an agricultural soil moisture meter is provided having a sensor and cable management system. The sensor and cable management system may proficiently store a soil moisture sensor and cable while also providing quick access to the same. The case also includes an integrated rod that enables a user to prop the moisture meter at a desired angle relative to the ground.

9 Claims, 10 Drawing Sheets

(56) References Cited

U.S. PATENT DOCUMENTS

| | | | |
|---|---|---|---|
| 2021/0391678 A1* | 12/2021 | Carnevali | ............ H04B 1/3888 |
| 2022/0248617 A1 | 8/2022 | Buss | |
| 2023/0045485 A1* | 2/2023 | Carnevali | .............. H02J 7/731 |
| 2023/0094121 A1 | 3/2023 | Eddaoudi et al. | |
| 2023/0341897 A1* | 10/2023 | Carnevali | ............ G06F 1/1632 |

* cited by examiner

PROTECTIVE CASE FOR SOIL MOISTURE METER

CROSS-REFERENCE TO RELATED APPLICATIONS

Not Applicable

FEDERAL SPONSORSHIP

Not Applicable

JOINT RESEARCH AGREEMENT

Not Applicable

TECHNICAL FIELD

The present invention relates generally to protective cases for electronic devices. More particularly, the present invention relates to a non-intrusive moisture meter protective case having a sensor support section and a sensor cable management section. The sensor and cable management sections allow a user to proficiently store a soil moisture sensor and cable with a corresponding moisture meter while also providing quick access to the same. Further, the robust and protective case shields the moisture meter from sometimes harsh agricultural settings while allowing easy user access to the moisture meter display and electronic ports and switches.

BACKGROUND

Handheld electronic devices used outdoors must be able to function reliably while withstanding often encountered harsh environment conditions. Even durable devices made from robust materials may fail a farmer or crop grower when subjected to the unforgiving and uncompromising demands frequently found in the agricultural fields.

By way of example, a grower may wish to carry a field probe, corresponding electronic device and electronic tethering cables into the field. However, the external housing of electronic devices used in the agricultural field may shatter or sustain damage from an unintended impact. The damage from impact may result in a cracked screen, fragmented housings, and/or failed or malfunctioning electrical components. Protecting the handheld electronic device, probe and cable carried into the agricultural field may be accomplished by using a padded carrying case or briefcase to reduce potential damage from unintentional drops or other impacts. However, padded carrying cases are bulky, require removal of the electronic device from the case to use the device, and contradict a consumer's desire for a compact mobile electronic device.

Additionally, a grower may want to increase the functionality of a protective case by adding practical structures to the case, however these added structures typically further add bulk and weight to the case. An increase in bulk or weight may result in a cumbersome and less desirable case. Accordingly, there is a need to provide a protective case for handheld agricultural electronic devices that minimize the bulkiness and weight of the case while maintaining impact protection and additional versatility.

SUMMARY

Embodiments according to aspects of the present invention provide a protective covering for a handheld soil moisture meter or other handheld agricultural electronic device that absorbs shock while also providing a system for soil moisture meter probe storage and cable management. The protective case for an agricultural electronic device, in accordance with aspects of the present invention, may include a pliable body adapted for receiving the agricultural device and a holder member adapted for receiving ancillary components of the agricultural device. In an exemplary embodiment of the present invention the agricultural device consists of a soil moisture meter and the ancillary components include a TDR moisture sensor and a connecting data cable. The pliable body of the protective case has a first side and opposing second side. The first side of the pliable body has a cavity formed into the side of the pliable body, wherein the first cavity is adapted for receiving the soil moisture meter. The second side of the pliable body has a holder member extending outwardly from the second side of the pliable body. The holder member is adapted for retaining the soil moisture sensor. Additionally, the holder member is adapted for retaining the data cable of the soil moisture sensor.

In embodiments of the invention, a rod coupler adapted for coupling a rod to the protective case is incorporated into the protective case. The rod is adapted for fixing the protective case and soil moisture meter contained therein in a vertical orientation relative to the ground. A top and bottom end of the pliable body of the protective case has cut out openings in the top and bottom ends. The cutout openings provide access to electronic ports and power switches of the soil moisture meter. Also, the holder member may include guide channels formed in the holder member wherein the guide channels are adapted for receiving prongs of the TDR soil moisture sensor. Drain channels may be formed in the holder member adjacent and intersecting the guide channels to reduce moisture residing in the prong guide channels. The holder member may include a tab extending outward and downward from the top end of the holder member, wherein the tab is adapted to retain the moisture sensor within the holder member.

In accordance with other aspects of the invention, an embodiment of the invention includes a protective case for an agricultural electronic device. The protective case has a pliable body, a holder member extending from a back portion of the pliable body and a tab extending from a top portion of the holder member. The pliable body has a first side and opposing second side, wherein the pliable body has a cavity formed into the first side of the pliable body. The first cavity is adapted for receiving an agricultural electronic device such as a soil moisture meter. The top and bottom end of the pliable body has cut out openings in the top and bottom ends that provide access to the top and bottom ends of the soil moisture meter. The tab extends outward and downward from the holder member. The tab is adapted to retain the soil moisture sensor within the a slot formed in the holder member for the main body of the moisture sensor. The holder member extends outwardly from the second side of the pliable body. The holder member is adapted for retaining the soil moisture sensor and a cable of the soil moisture sensor. The holder member further includes guide channels formed in the holder member wherein the guide channels are adapted for receiving prongs of a TDR soil moisture sensor.

Embodiments in accordance with these aspects of the invention may further include a rod coupler adapted for coupling a rod to the pliable body of the protective case. The rod may be fixed in the ground to orient the protective case and moisture meter contained therein in a vertical orientation. The holder member may further include drain channels formed in the holder member adjacent and intersecting the guide channels. The drain channels allow moisture to drain out of the guide channels. Further, depending upon the length of the prongs of the TDR sensor, tips of the prongs may extend out of the drain channels.

The accompanying drawings, which are incorporated in and constitute a portion of this specification, illustrate embodiments of the invention and, together with the detailed description, serve to further explain the invention. The embodiments illustrated herein are presently preferred; however, it should be understood, that the invention is not limited to the precise arrangements and instrumentalities shown. For a fuller understanding of the nature and advantages of the invention, reference should be made to the detailed description in conjunction with the accompanying drawings.

DESCRIPTION OF THE DRAWINGS

In the various figures, which are not necessarily drawn to scale, like numerals throughout the figures identify substantially similar components.

DETAILED DESCRIPTION

Figure 1:
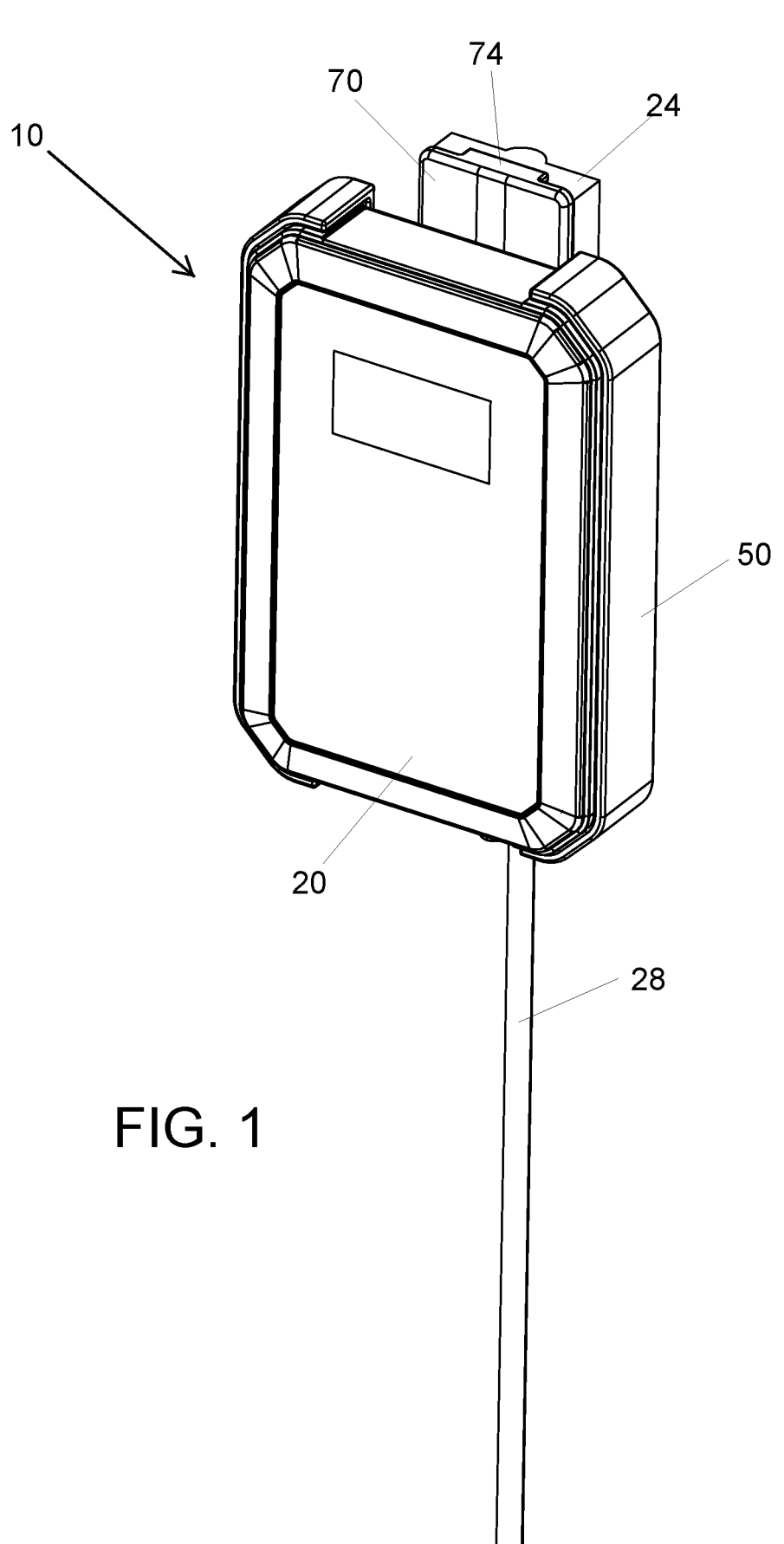
FIG. 1 is a front top perspective view of a protective case in accordance with the present invention shown in use with a soil moisture meter contained therein.
Figure 2:
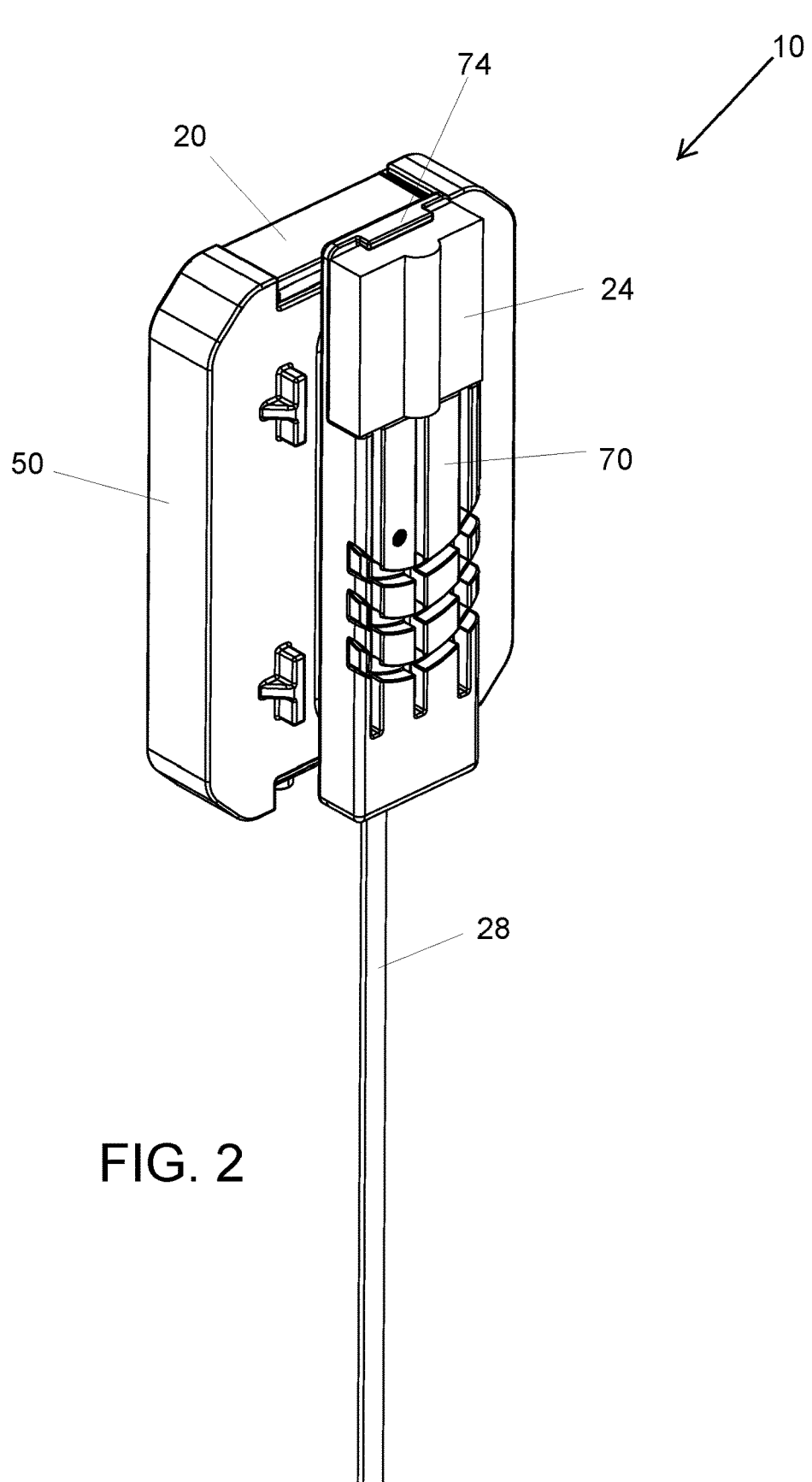
FIG. 2 is a back top perspective view of a protective case in accordance with the present invention shown in use with a soil moisture meter contained therein.
Figure 3:
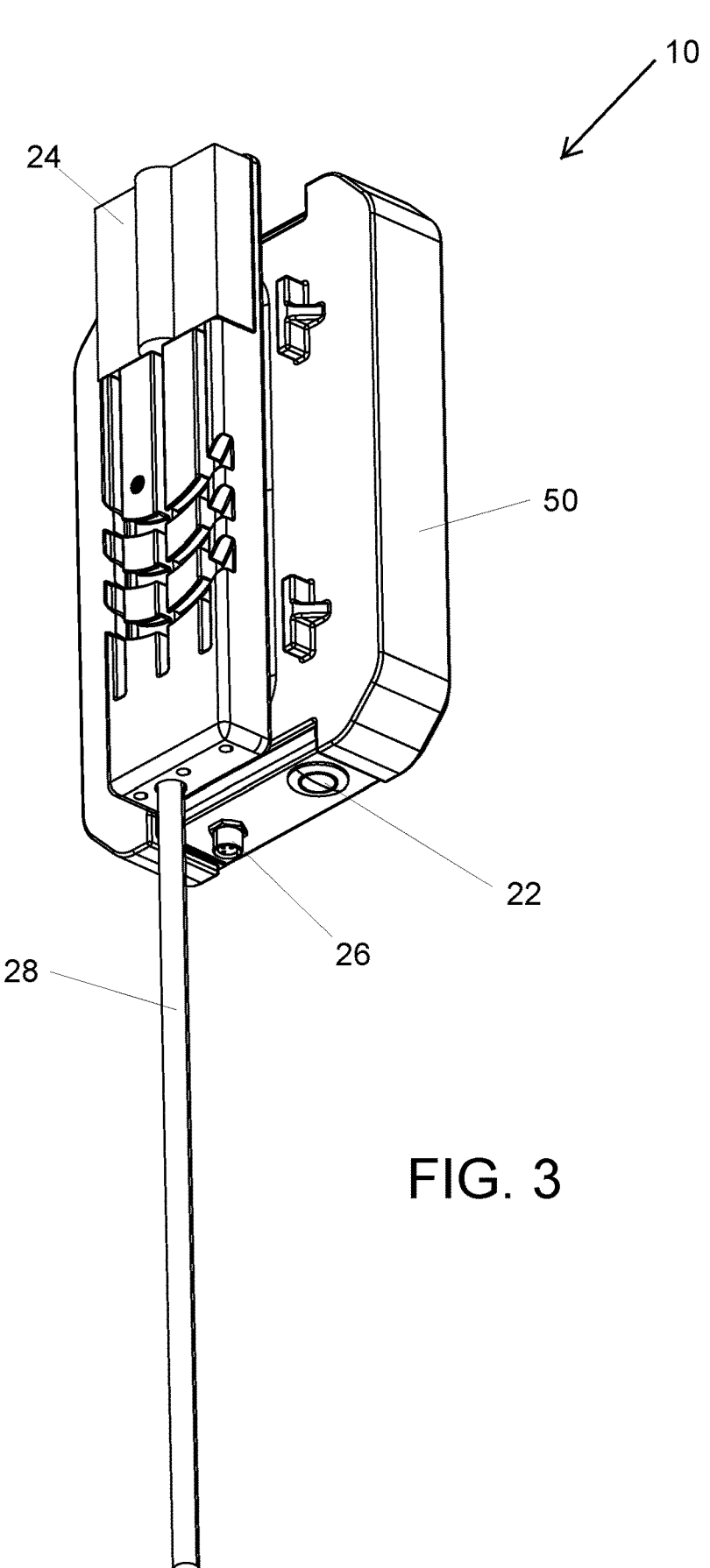
FIG. 3 is a back bottom perspective view of a protective case in accordance with the present invention shown in use with a soil moisture meter contained therein.

The following description provides detail of various embodiments of the invention, one or more examples of which are set forth below. Each of these embodiments are provided by way of explanation of the invention, and not intended to be an undue limitation of the invention. Further, those skilled in the art will appreciate that various modifications and variations may be made in the present invention without departing from the scope or spirit of the invention. By way of example, those skilled in the art will recognize that features illustrated or described as part of one embodiment, may be used in another embodiment to yield a still further embodiment. Thus, it is intended that the present invention also cover such modifications and variations that come within the scope of the appended claims and their equivalents.

In an embodiment of the invention a protective case 10 is provided that minimizes the bulkiness and weight of the protective case for a moisture meter 20, while providing a storage and cable management system for a soil moisture sensor 24 and cable 32. The protective covering 10 for the moisture meter 20 is configured to be user removable from the moisture meter, wherein the case has a front and back such that a cavity is formed in the front side of the protective case and is adapted for receiving and containing the moisture meter therein. The protective case is made from a pliable material to allow the sloped cavity sidewalls to bend outward to allow the meter to be inserted between the sidewalls. The pliable body then conforms to the outer sides of the moisture meter.

With reference to the Figures various aspects of the invention will be further described. FIGS. 1-3 and 7-10 illustrates an exemplary handheld agricultural electronic device or moisture meter 20 inserted and contained within the protective case or covering 10 of the present invention. Those skilled in the art will appreciate that the length, width and thickness of the components of the protective cover 10 may be modified to accommodate various handheld electronic devices. The 10 case includes a pliable body 50 having cutouts 66 formed in top and bottom ends of the case 10. The cutouts expose top and bottom ends of the moisture meter 20 allowing a user access to power switch 22 and cable coupling 26. The pliable body has first and second sides 54 and 58 respectively, wherein a cavity 62 having sloping pliable sidewalls 64 is formed in the first side 54 of the pliable body. The cavity 62 is adapted for receiving the moisture meter 20 therein. An outer perimeter portion of the sloping sidewall 64 may be constructed to overlap the front outer edge of the moisture meter 20 to further retain the meter 20 within the cavity 62.

The back or second side of the pliable body includes a holder member 70 extending outward from the back side of the pliable body. A bottom of the holder member 70 includes an aperture or coupling 90 extending into the holder member 70. The aperture 90 is adapted for receiving a rod 28. The rod may be used to fix the meter 20 in a vertical orientation relative to the ground. A top portion of the holder member 70 has a slot 72 formed therein that is sized to retain the main body portion of a soil moisture sensor 24. A tab 74 extends outward and downward from a top portion of the holder member 70. The tab 74 is pliable and bends out of the way when the moisture meter is inserted within slot 72 but then bends back and retains the moisture meter within the slot of the holding member 70.

The holder member 70 further includes longitudinal channels 76 extending into the main body of the holder member 70. The channels are sized and spaced apart such that prongs 30 of the soil moisture sensor 24 insert into the channels 76. The holder member 70 may further include drain channels 78 extending through the holder member from the prong channels 76 to a bottom of the channel holding member 70. In this manner, liquid or moisture that accumulate in the prong channels 76 may drain out the bottom of the holding member 70. Additionally, the holding member 70 includes arced channels 80 formed in the holding member. Cable 32 coupled with the moisture sensor 24 may be routed within the arced channels 80 and between the holding member 70 and pillars 84 extending outward from the back side 58 of the pliable body 50.

Figure 4:
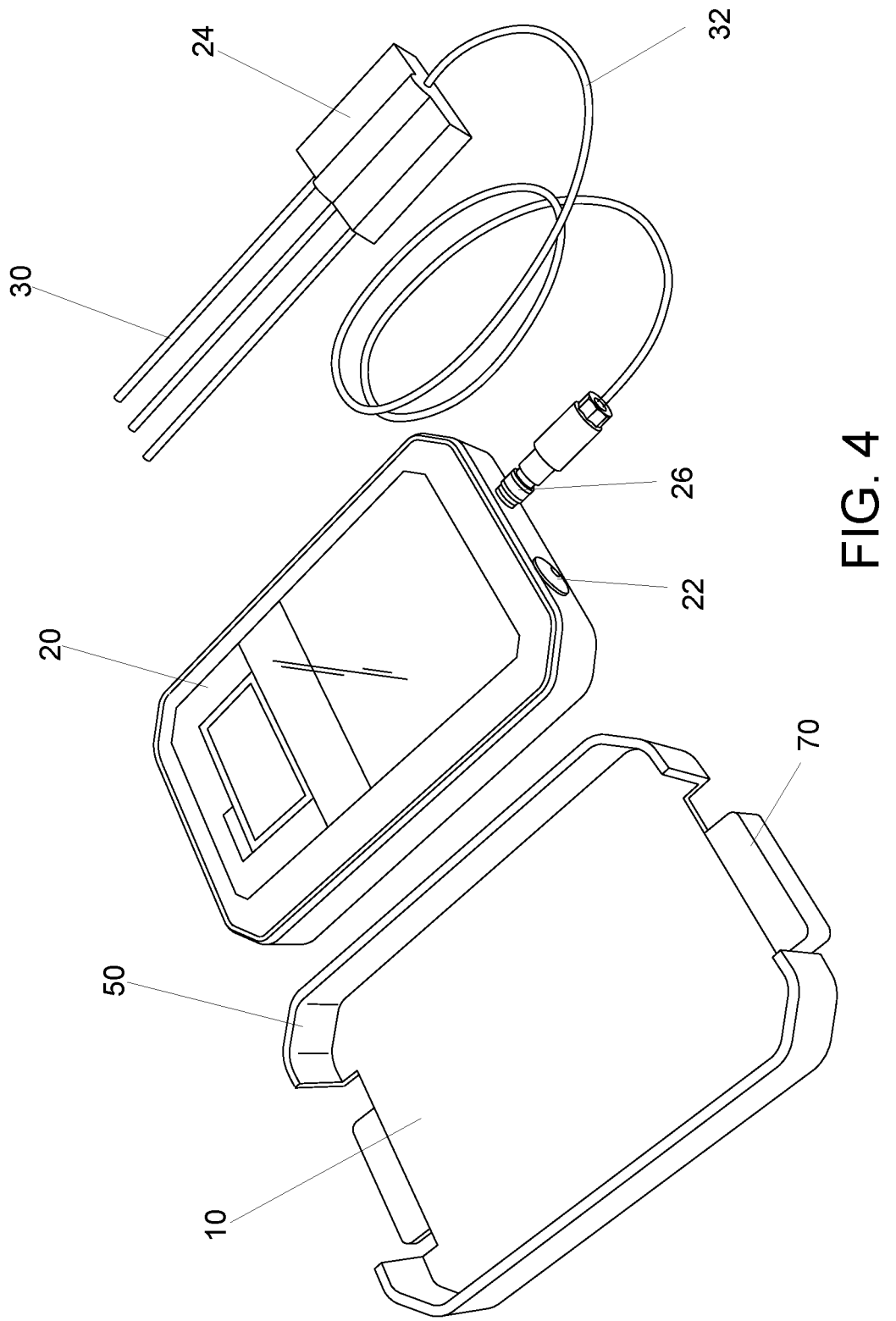
FIG. 4 is a front perspective view of a protective case in accordance with the present invention shown with a soil moisture meter and probe removed from the case.
Figure 5:
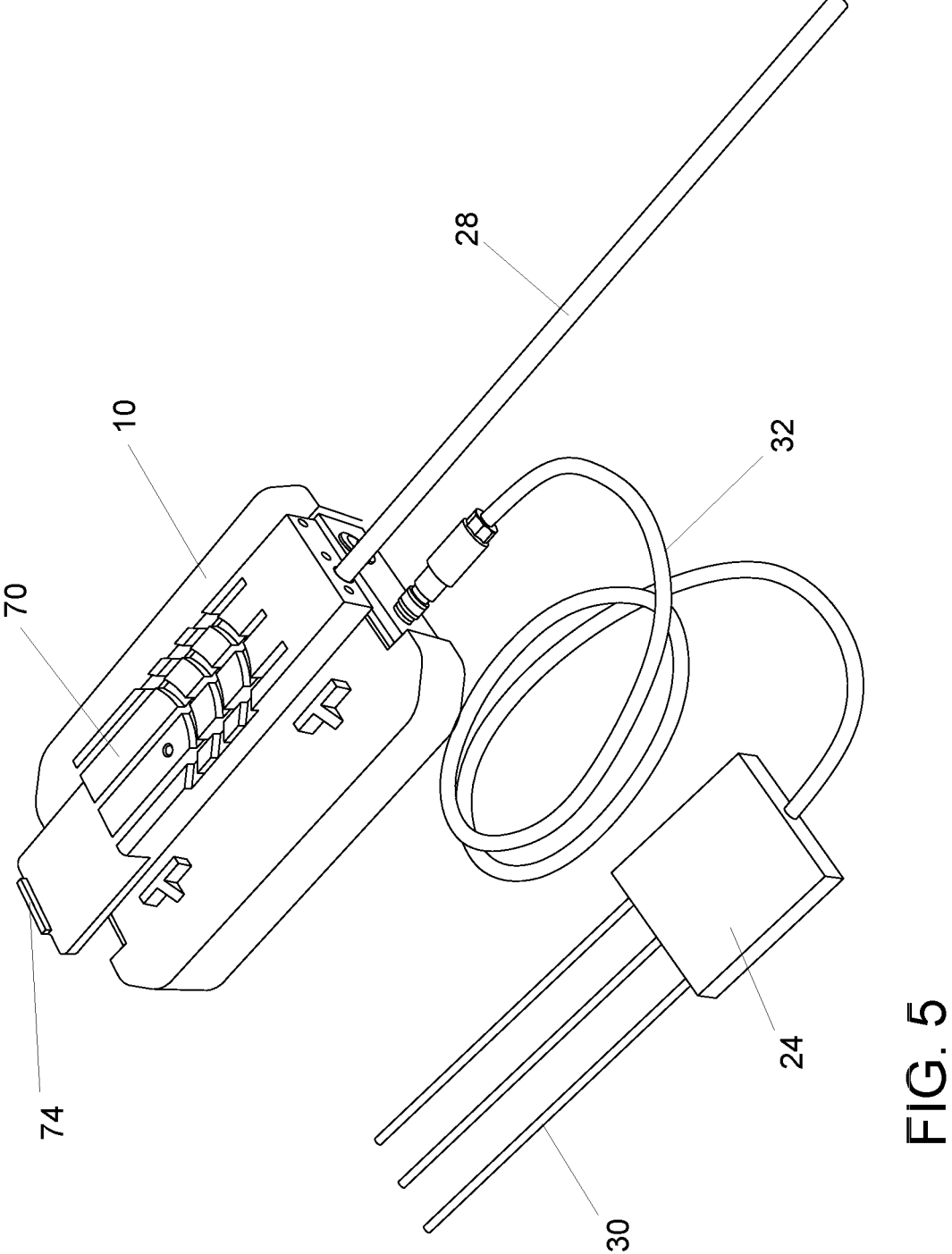
FIG. 5 is a back perspective view of a protective case in accordance with the present invention shown in use with a soil moisture meter contained therein and a soil moisture probe electronically coupled to the moisture meter.
Figure 6:
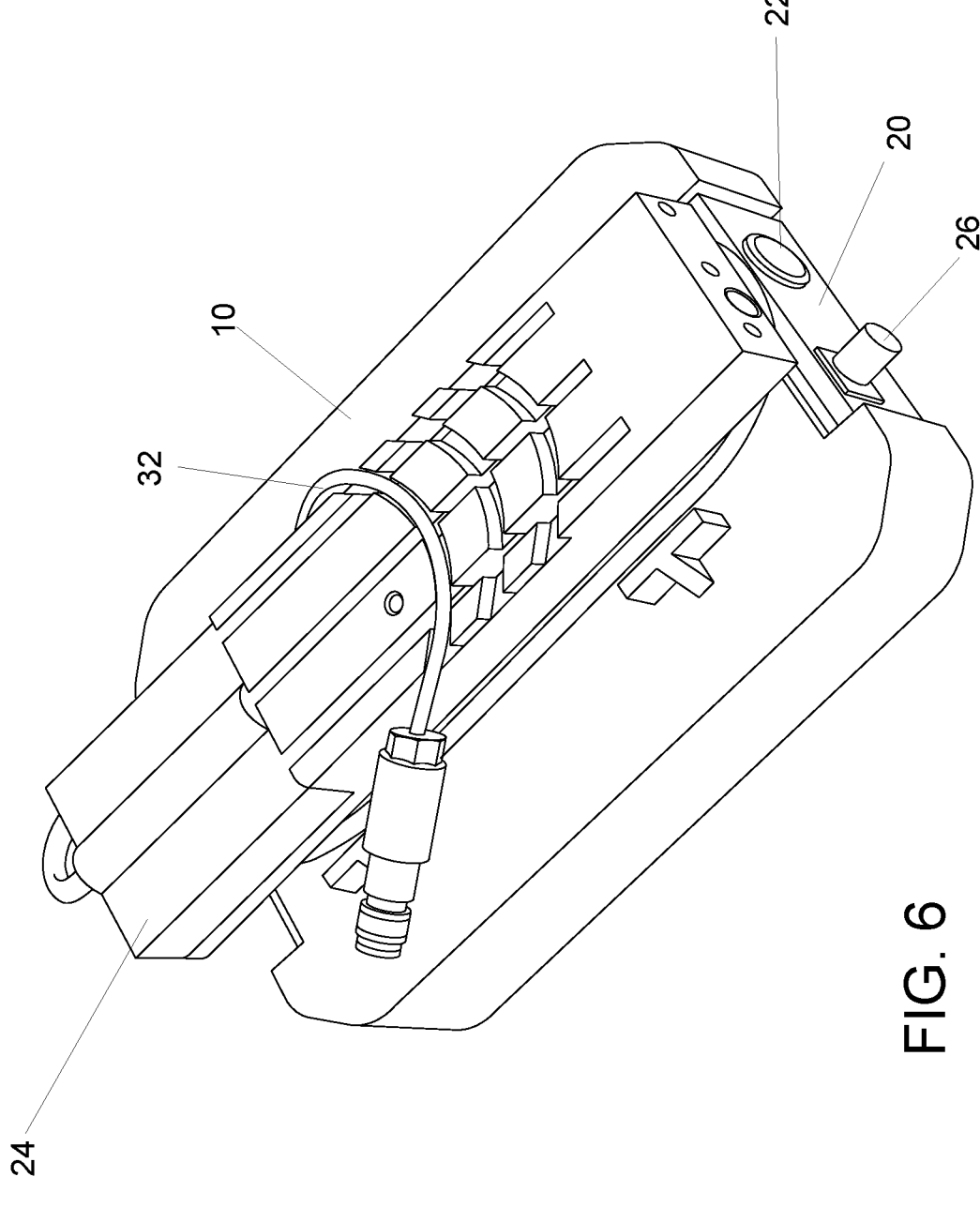
FIG. 6 is a back perspective view of a protective case in accordance with the present invention shown with a soil moisture meter contained therein and the probe and cable in a stowed position.
Figure 7:
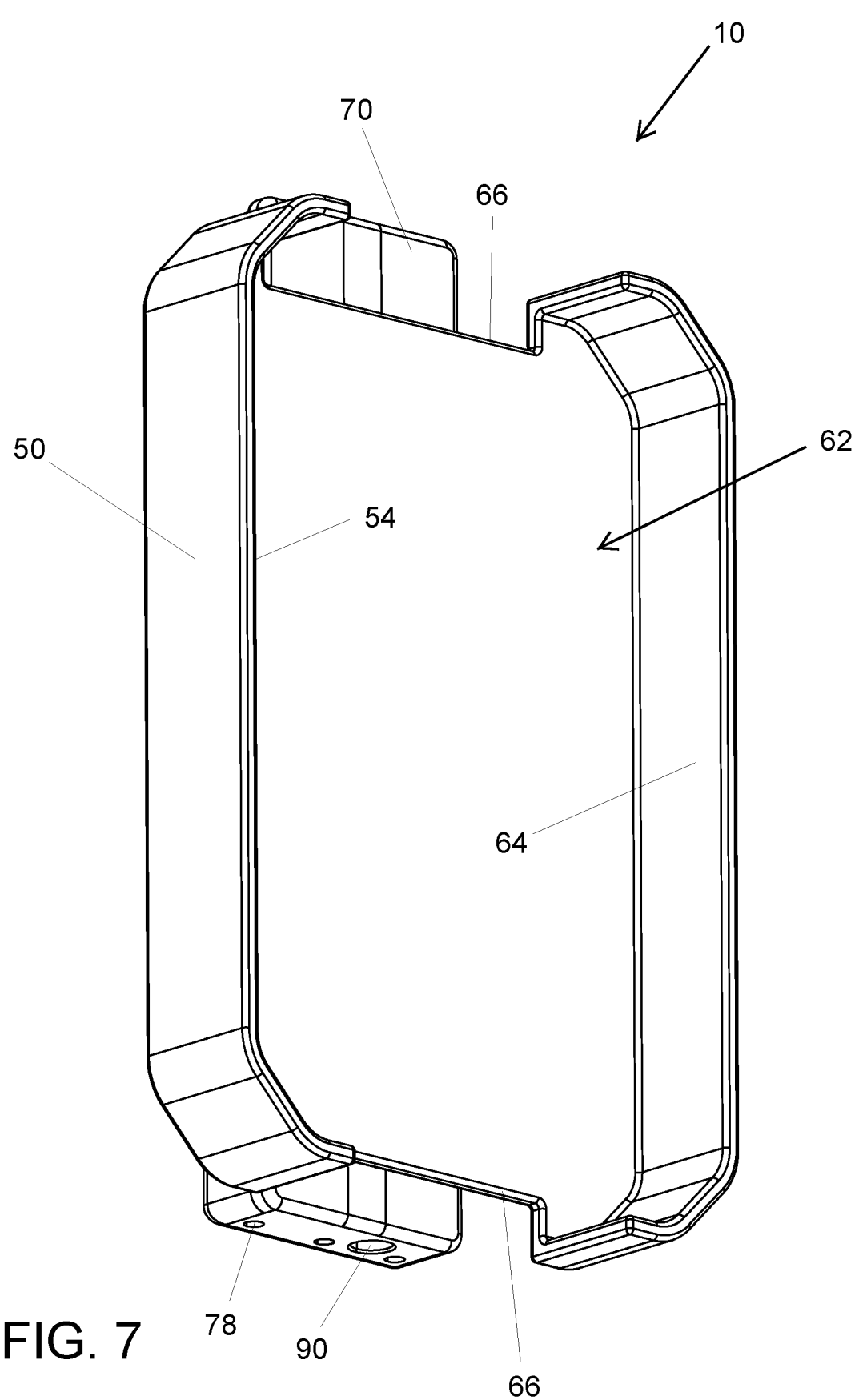
FIG. 7 is a front side perspective view of a protective case in accordance with the present invention.
Figure 8:
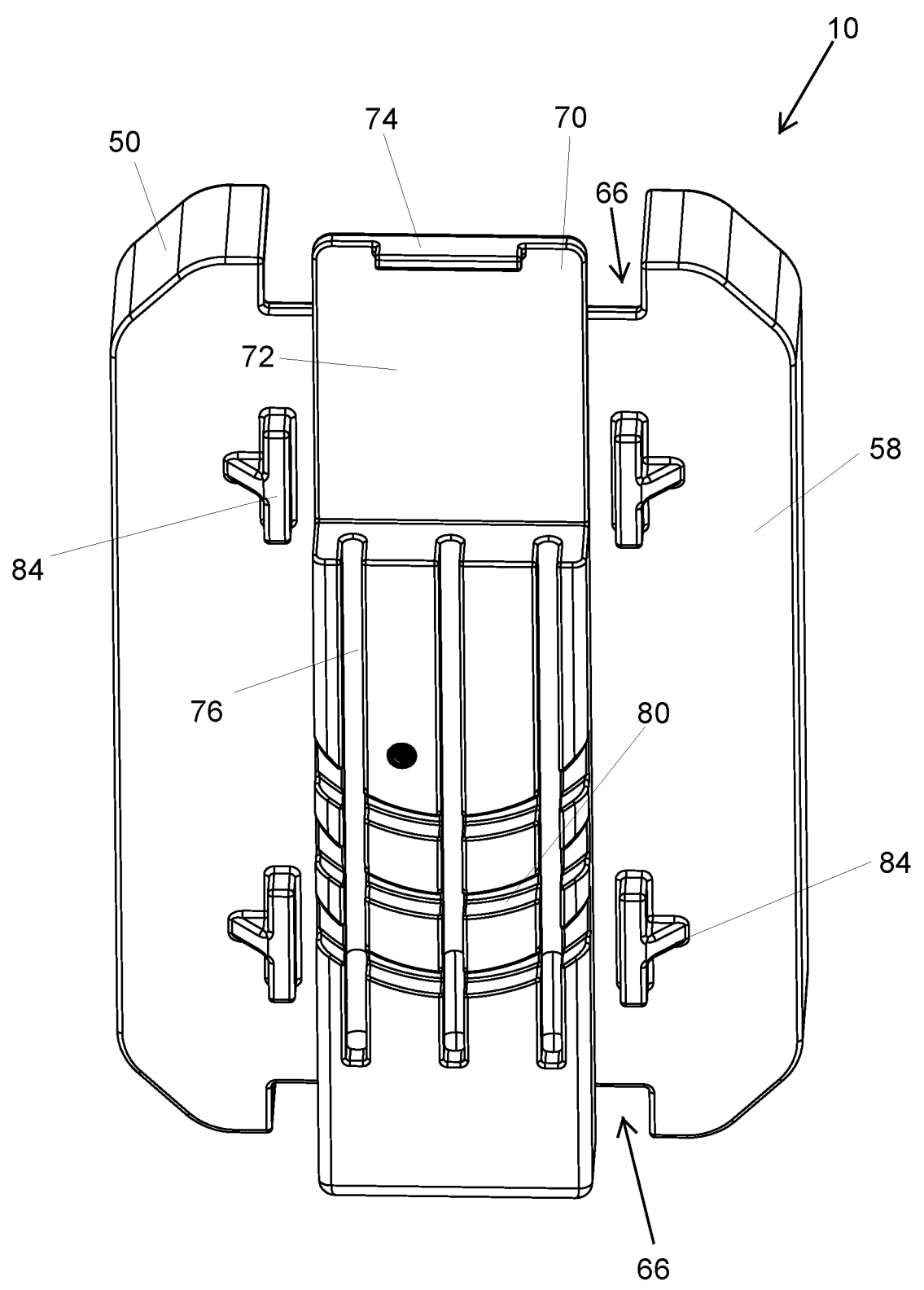
FIG. 8 is a back upper perspective view of a protective case in accordance with the present invention.
Figure 9:
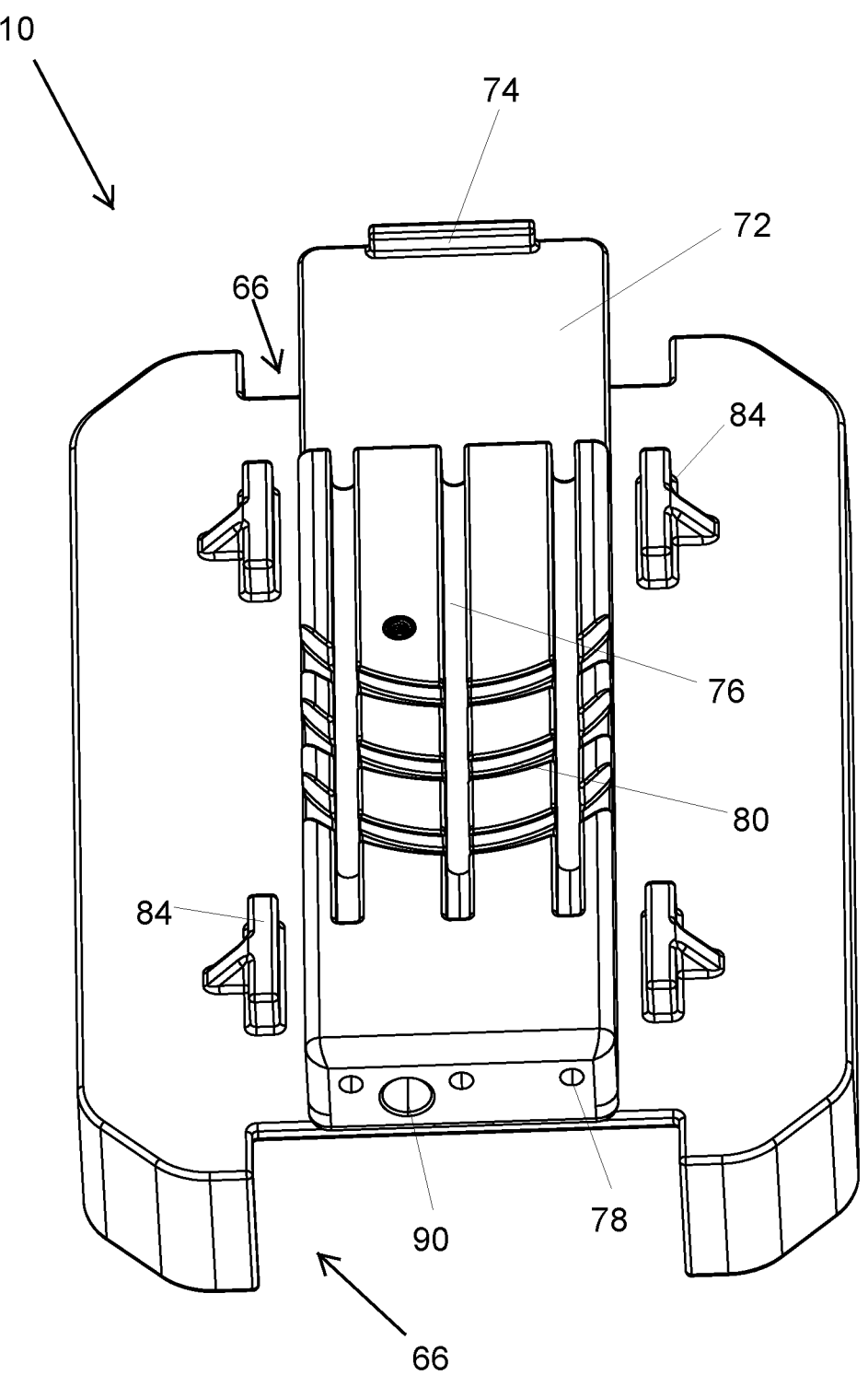
FIG. 9 is a back lower perspective view of a protective case in accordance with the present invention.
Figure 10:
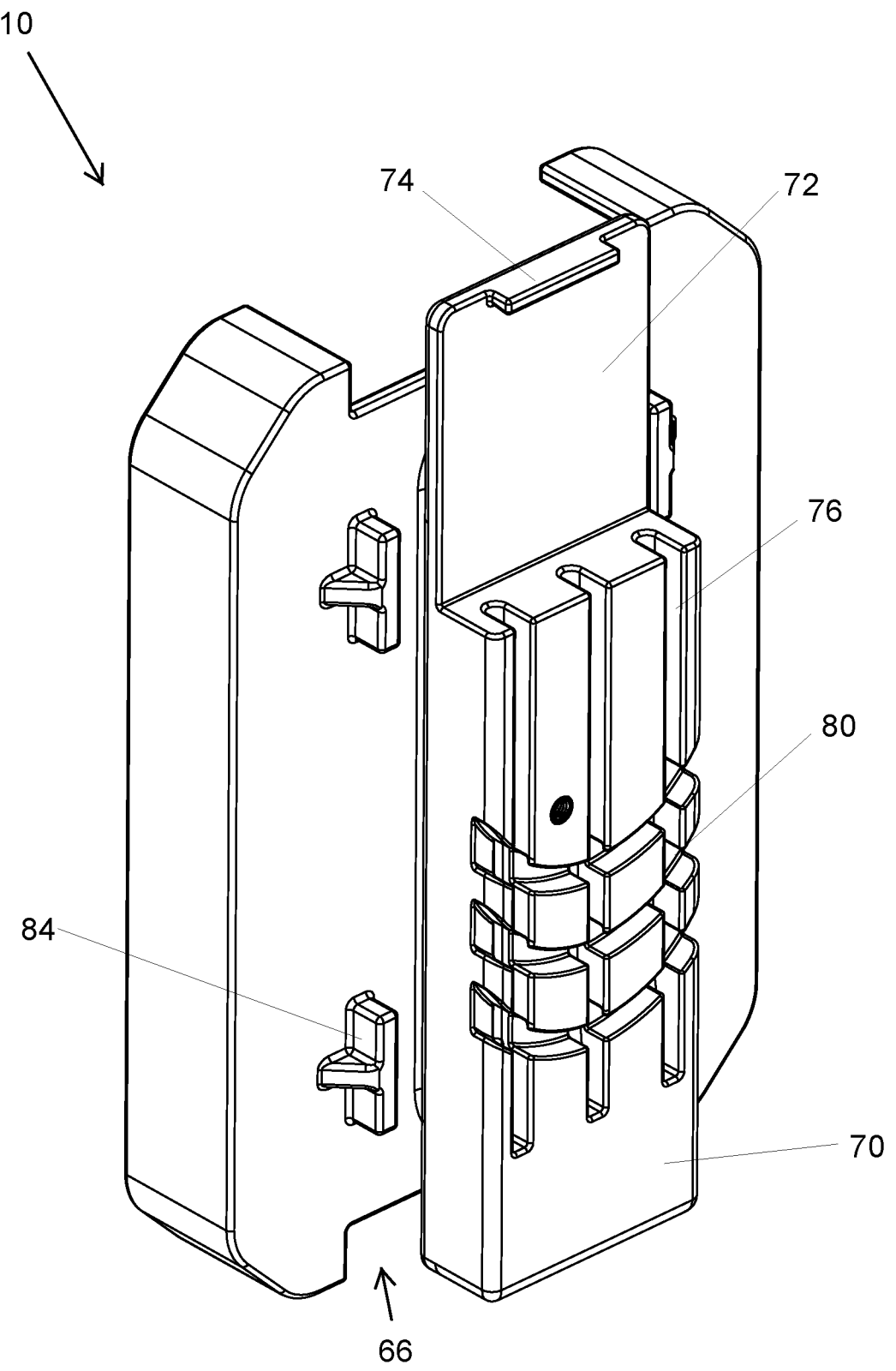
FIG. 10 is a back side perspective view of a protective case in accordance with the present invention.

FIGS. 4-6 further illustrates how the moisture meter 20 is contained within the pliable body 50 and how the case 10 contains a moisture meter 20, sensor 24 and cable 32. The meter 20 is retained in cavity 62 and held within the case 10 by the sloping sidewalls 64 of the pliable body 50. The moisture meter is electronically tethered or linked to the moisture meter 20 with cable 32. The user may press a free end of rod 28 into the ground to fix the meter in an upright position. The user may also press the prongs 30 of the moisture sensor 24 into the ground such that moisture of the soil may be used to monitor moisture levels of the soil. When not in use, the rod may be removed from aperture 90 and the cable 32 may be routed through channels 80 and wound between the pillars 84 and holding member 70. Further, the prongs 30 may be guided into the prong channels 76 and the body of the moisture sensor 24 may be snapped into storage position within the slot 72. In this manner, the cable is managed without removing from the moisture sensor 24 and meter 20 or dangling from the sensor 24.

The various embodiments described herein are illustrative of the present invention and not limiting as to the scope and spirit of the present invention. These and various other aspects and features of the invention are described with the intent to be illustrative, and not restrictive. This invention has been described herein with detail in order to comply with the patent statutes and to provide those skilled in the art with information needed to apply the novel principles and to construct and use such specialized components as are required. It is to be understood, however, that the invention can be carried out by specifically different constructions, and that various modifications, both as to the construction and operating procedures, can be accomplished without departing from the scope of the invention. Further, in the appended claims, the transitional terms comprising and including are used in the open-ended sense in that elements in addition to those enumerated may also be present. Other examples will be apparent to those of skill in the art upon reviewing this document.

The following claims are incorporated into this description.

The invention claimed is:

1. A protective case for an agricultural electronic device, the case comprising:

a pliable body having a first side and opposing second side, wherein the pliable body has a cavity formed into the first side of the pliable body, and further wherein the cavity is adapted for receiving an agricultural electronic device; and a holder member extending outwardly from the second side of the pliable body, wherein the holder member is adapted for retaining a soil moisture sensor and further wherein the holder member is adapted for retaining a cable of the soil moisture sensor.

2. The protective case as recited in claim 1, further including a rod coupler adapted for coupling a rod to the case to thereby fix the case in ground in a vertical orientation.

3. The protective case as recited in claim 1, wherein a top and bottom end of the pliable body has cut out openings in the top and bottom ends.

4. The protective case as recited in claim 1, wherein the holder member includes guide channels formed in the holder member wherein the guide channels are adapted for receiving prongs of the soil moisture sensor of a TDR sensor type.

5. The protective case as recited in claim 4, wherein the holder member further includes drain channels formed in the holder member adjacent and intersecting the guide channels.

6. The protective case as recited in claim 3, further including a tab extending outward and downward from the top end of the holder member, wherein the tab retains the soil moisture sensor within the holder member.

7. A protective case for an agricultural electronic device, the case comprising:

a pliable body having a first side and opposing second side, wherein the pliable body has a cavity formed into the first side of the pliable body, and further wherein the first cavity is adapted for receiving an agricultural electronic device, and further wherein a top and bottom end of the pliable body has cut out openings in the top and bottom ends;

a holder member extending outwardly from the second side of the pliable body, wherein the holder member is adapted for retaining a cable of a soil moisture sensor, and further wherein the holder member includes guide channels formed in the holder member wherein the guide channels are adapted for receiving prongs of the soil moisture sensor; and a tab extending outward and downward from the top end of the holder member, wherein the tab is adapted to retain the soil moisture sensor within the holder member.

8. The protective case as recited in claim 7, further including a rod coupler adapted for coupling a rod to the case to thereby fix the case with ground in a vertical orientation.

9. The protective case as recited in claim 7, wherein the holder member further includes drain channels formed in the holder member adjacent and intersecting the guide channels.

* * * * *